United States Patent [19]

Morgan et al.

[11] Patent Number: 5,520,980
[45] Date of Patent: May 28, 1996

[54] PROTECTIVE BARRIER APPAREL FABRIC

[75] Inventors: Linda J. Morgan; Robert D. Harris, Jr., both of Dunwoody, Ga.

[73] Assignee: Kimberly-Clark Corporation, Neenah, Wis.

[21] Appl. No.: 189,219

[22] Filed: Jan. 31, 1994

[51] Int. Cl.⁶ ............................................. B32B 7/00
[52] U.S. Cl. ..................... 428/246; 428/253; 428/297; 428/298; 428/302
[58] Field of Search ............................... 428/287, 224, 428/288, 903, 246, 253

[56] References Cited

U.S. PATENT DOCUMENTS

| | | | |
|---|---|---|---|
| 3,410,748 | 11/1968 | Blue | 161/76 |
| 3,576,703 | 4/1971 | Baker et al. | 161/77 |
| 3,676,242 | 7/1972 | Prentice | 156/62.4 |
| 3,692,618 | 9/1972 | Dorschner et al. | 161/72 |
| 3,849,241 | 11/1974 | Butin et al. | 161/169 |
| 4,194,041 | 3/1980 | Gore et al. | 428/315 |
| 4,194,940 | 3/1980 | Damico et al. | 156/331 |
| 4,296,163 | 10/1981 | Emi et al. | 428/212 |
| 4,307,143 | 12/1981 | Meitner | 252/91 |
| 4,340,563 | 7/1982 | Appel et al. | 264/518 |
| 4,344,999 | 8/1982 | Gohlke | 428/212 |
| 4,379,192 | 4/1983 | Wahlquist et al. | 428/156 |
| 4,426,421 | 1/1984 | Nakamae et al. | 428/234 |
| 4,443,511 | 4/1984 | Worden et al. | 428/198 |
| 4,526,828 | 7/1985 | Fogt et al. | 428/229 |
| 4,555,811 | 12/1985 | Shimalla | 2/51 |
| 4,663,220 | 5/1987 | Wisneski et al. | 428/221 |
| 4,692,368 | 9/1987 | Taylor et al. | 428/137 |
| 4,707,398 | 11/1987 | Boggs | 428/224 |
| 4,720,415 | 1/1988 | Vander Wielen et al. | 428/287 |
| 4,736,467 | 4/1988 | Schwarze et al. | 2/114 |
| 4,741,949 | 5/1988 | Morman et al. | 428/224 |
| 4,761,324 | 8/1988 | Rautenberg et al. | 428/198 |
| 4,801,482 | 1/1989 | Goggans et al. | 428/68 |
| 4,803,117 | 2/1989 | Daponte | 428/228 |
| 4,857,393 | 8/1989 | Kato et al. | 428/289 |
| 4,868,928 | 9/1989 | Norvell | 2/272 |
| 4,877,679 | 10/1989 | Leatherman et al. | 428/224 |
| 4,891,957 | 1/1990 | Strack et al. | 66/192 |
| 4,929,492 | 5/1990 | Carey, Jr. et al. | 428/198 |
| 4,935,287 | 6/1990 | Johnson et al. | 428/198 |
| 4,943,475 | 7/1990 | Baker et al. | 428/246 |
| 4,969,998 | 11/1990 | Henn | 210/490 |
| 4,970,259 | 11/1990 | Mitchell et al. | 524/505 |
| 5,001,785 | 3/1991 | Heiman et al. | 2/123 |
| 5,007,112 | 4/1991 | Lewis, Jr. et al. | 2/79 |
| 5,026,591 | 6/1991 | Henn et al. | 428/198 |
| 5,032,450 | 7/1991 | Rechlicz et al. | 428/196 |
| 5,036,551 | 8/1991 | Dailey et al. | 2/167 |
| 5,061,258 | 10/1991 | Martz | 604/307 |
| 5,098,770 | 3/1992 | Paire | 428/198 |
| 5,183,702 | 2/1993 | Taylor et al. | 428/266 |
| 5,236,769 | 8/1993 | Paire | 428/196 |
| 5,332,613 | 7/1994 | Taylor et al. | 428/152 |

FOREIGN PATENT DOCUMENTS

| | | |
|---|---|---|
| 0233995 | 1/1986 | European Pat. Off. . |
| 0311316 | 4/1989 | European Pat. Off. . |
| 0391661 | 10/1990 | European Pat. Off. . |

OTHER PUBLICATIONS

B. F. Goodrich: "Estaine® Resins for Textile Coating": BFGC–E Aug. 1984.

Sueo Kawabata:"The Standardization and Analysis of Hand Evaluation (2nd Edition)" Chapter IV, pp. 28–70: Jul. 1980.

*Primary Examiner*—George F. Lesmes
*Assistant Examiner*—Helen F. Lee
*Attorney, Agent, or Firm*—James B. Robinson

[57] ABSTRACT

There is provided a protective barrier apparel fabric comprised of an at least three layer laminate. The first layer being of elastomeric meltblown thermoplastic polymer web, the second layer of a liquid impermeable film and the third layer of liquid permeable material, where the layers are bonded together. The elastomeric meltblown layer may be stitch-bonded prior to incorporation into the laminate and/or may be saturated with a latex composition prior to incorporation into the laminate. The laminate provides good MVTR and protection against blood strikethrough.

2 Claims, No Drawings

PROTECTIVE BARRIER APPAREL FABRIC

BACKGROUND OF THE INVENTION

This invention relates to the field of fabrics for durable use as protective apparel.

Protective fabrics having barrier properties are desirable in a number of applications. For example, such fabrics are useful in surgical gowns for protecting medical personnel from contact with blood or other body fluids during surgery in order to help prevent the spread of disease. In such uses, it is desirable that the fabric perform its function in a manner which is comfortable and that the fabric conform relatively well to the wearer's body. A stiff or heavy fabric which did not drape well would be uncomfortable and might undesirably restrict the movement of the wearer.

It is also desirable that such protective fabrics have the ability to be washed and reused a number of times while retaining to a large degree such barrier properties. Reusability is becoming more and more important in such uses because of the rising cost of disposing of articles contaminated with bodily fluids. Reducing the volume of contaminated material needing disposal would have a very desirable economic and environmental impact.

Accordingly, it is an object of this invention to provide a protective barrier apparel fabric which has good drape and body conformance and which may be laundered and reused a number of times.

SUMMARY

The objects of the invention are provided by a protective barrier apparel fabric comprised of an at least three layer laminate. The first layer being of elastomeric meltblown thermoplastic polymer web, the second layer of a liquid impermeable film and the third layer of liquid permeable material, where the layers are bonded together. The elastomeric meltblown layer may be stitchbonded prior to incorporation into the laminate and/or may be saturated with a latex composition prior to incorporation into the laminate.

DETAILED DESCRIPTION

Definitions

As used herein the term "nonwoven fabric or web" means a web having a structure of individual fibers, filaments or threads which are interlaid, but not in an identifiable manner. Nonwoven fabrics or webs have been formed from many processes such as for example, meltblowing processes, spunbonding processes, and bonded carded web processes.

As used herein the term "microfibers" means small diameter fibers having an average diameter not greater than about 100 microns, for example, having an average diameter of from about 0.5 microns to about 50 microns, or more particularly, microfibers may desirably have an average diameter of from about 2 microns to about 40 microns.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Meltblowing is well known in the art and is described, for example, in U.S. Pat. No. 3,849,241 to Butin, U.S. Pat. No. 4,307,143 to Meitner et al., and U.S. Pat. No. 4,707,398 to Wisneski et al.

As used herein the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al.

As used herein the term "bicomponent" refers to fibers which have been formed from at least two polymers extruded from separate extruders but spun together to form one fiber. The configuration of such a bicomponent fiber may be, for example, a sheath/core arrangement wherein one polymer is surrounded by another or may be a side by side arrangement.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have been elongated 50 percent and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the terms "elastic" and "elastomeric" mean any material which, upon application of a biasing force, is stretchable to a stretched, biased length which is at least about 125 percent (that is at least about one and one quarter) of its relaxed, unbiased length and which will recover at least about 40 percent of its stretch or elongation upon release of the stretching, elongating force. An example which would satisfy this definition of an elastic or elastomeric material would be a one inch sample of a material which is elongatable to at least 1.25 inches and which, upon being elongated to 1.25 inches and released, will return to a length of not more than 1.15 inches. Many elastic materials may be stretched by much more than 25 percent of their relaxed length, for example 100 percent or more, and many of these will return to substantially their original relaxed length, for example, to within 105 percent of their original relaxed length upon release of the stretching, elongating force.

As used herein, the term "stitchbonded" means, for example, the stitching of a material in accordance with U.S. Pat. No. 4,891,957 to Strack et al.

As used herein, the term "garment" means any type of apparel which may be worn. This includes diapers, training pants, incontinence products, surgical gowns, face masks, head coverings, industrial work wear and coveralls, undergarments, pants, shirts, jackets, gloves, socks, shoe coverings, and the like.

As used herein, the term "barrier fabric" means a fabric which is relatively impermeable to the transmission of fluids, i.e., a fabric which has blood strikethrough rate of 1.0 or less according to ASTM test method 22.

Protective barrier fabrics are desirable in producing such items as surgical gowns and drapes which will protect the wearer from contact with the bodily fluids of another in order to avoid transmission of disease. The degree of protection required depends on the exact activity or type of surgery being performed which may require more or less of a barrier to fluids. Some surgeries (e.g. eye surgery) may require little protection of the personnel involved because the risk of contact with bodily fluids is generally low. Some procedures require relatively more and some procedures require the utmost protection for the medical personnel.

The laminate fabric of this invention comprises a layered construction of an elastomeric meltblown thermoplastic polymer, a continuous liquid impermeable film, and a liquid permeable material.

The elastomeric meltblown thermoplastic polymer useful in the practice of this invention may be those made from block copolymers such as polyurethanes, copolyether esters, ethylene vinyl acetates (EVA), copoly(styrene/ethylene-butylene) and the like. Generally, any suitable elastomeric fiber forming resins or blends containing the same may be utilized to form the nonwoven webs of elastomeric fibers of the invention. For example, useful elastomeric fiber forming resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated (A-B)$_m$-X, wherein X is a polyfunctional atom or molecule and in which each (A-B)$_m$- radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly(ethylene-butylene)/polystyrene) block copolymers available from the Shell Chemical Company of Houston, Tex. under the trade designation KRATON G. One such block copolymer may be, for example, KRATON® G-1657.

Other exemplary elastomeric materials which may be used to form an elastomeric nonwoven web include polyurethane elastomeric materials such as, for example, those available under the trademark ESTANE from B. F. Goodrich & Co., polyamide elastomeric materials such as, for example, those available under the trademark PEBAX from the Rilsan Company, and polyester elastomeric materials such as, for example, those available under the trade designation HYTREL® from E. I. DuPont De Nemours & Company. Formation of an elastomeric nonwoven web from polyester elastomeric materials is disclosed in, for example, U.S. Pat. No. 4,741,949 to Morman et al., hereby incorporated by reference. Elastomeric nonwoven webs may also be formed from elastomeric copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117. Particularly useful elastomeric meltblown thermoplastic webs are composed of fibers of a material such as disclosed in U.S. Pat. No. 4,707,398 to Boggs, U.S. Pat. No. 4,741,949 to Morman et al., and U.S. Pat. No. 4,663,220 to Wisneski et al. In addition, the elastomeric meltblown thermoplastic polymer layer may itself be composed of thinner layers of elastomeric meltblown thermoplastic polymer which have been sequentially deposited one atop the other or laminated together by methods known to those skilled in the art.

Boggs discloses a web made from a polyetherester having the general formula:

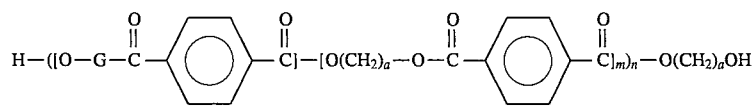

where "G" is selected from the group consisting of poly(oxyethylene)-alpha,omega-diol, poly(oxypropylene)-alpha,omega-diol, poly(oxytetramethylene)-alpha,omega-diol and "a", "m" and "n" are positive integers, and wherein said material has an elongation at break of from about 600 percent to 750 percent when measured in accordance with ASTM D-638 and a melt point of from about 350° F. to about 400° F. (176° to 205° C.) when measured in accordance with ASTM D-2117. Commercial examples of such materials are, for example, those known as Arnitel, formerly available from Akzo Plastics of Arnhem, Holland and now available from DSM of Sittard, Holland.

Morman et al. discloses a web made from a polyetherester having the general formula shown above wherein "G" is selected from the group consisting of poly(oxyethylene)-alpha,omega-diol, poly(oxypropylene)-alpha,omega-diol, poly(oxytetramethylene)-alpha,omega-diol and "a", "m" and "n" are positive integers. Commercial examples of such materials are, for example, those known as Hytrel which are available from E. I. duPont de Nemours of Wilmington, Del.

Wisneski et al. discloses a web including microfibers comprising at least about 10 weight percent of an A-B-A' block copolymer where "A" and "A'" are each a thermoplastic endblock which comprises a styrenic moiety and where "B" is an elastomeric poly(ethylene-butylene) midblock, and from greater than 0 weight percent up to about 90 weight percent of a polyolefin which when blended with the A-B-A' block copolymer and subjected to an effective combination of elevated temperature and elevated pressure conditions, is adapted to be extruded, in blended form with the A-B-A' block copolymer. Polyolefins useful in Wisneski et al. may be polyethylene, polypropylene, polybutene, ethylene copolymers, propylene copolymers, butene copolymers, and mixtures thereof. Commercial examples of such materials are, for example, those known as Kraton materials which are available from Shell Chemical Company of Houston, Tex.

The elastomeric meltblown layer may also be stitchbonded in accordance with U.S. Pat. No. 4,891,957 to Strack et al. Stitchbonding imparts strength and durability to the stitchbonded product and stitchbonding in the present invention is believed to impart increased abrasion resistance to the laminate. While stitchbonding generally is used to join two or more materials together, in this embodiment of the present invention the elastomeric meltblown layer is stitchbonded alone and then used in the fabrication of the laminate. Stitchbonding the entire laminate together, or stitchbonding the film layer to any other layer, would detrimentally affect the barrier properties of the laminate. Therefore, stitchbonding the elastomeric meltblown material prior to incorporation into the laminate preserves the desirable properties of the laminate.

The elastomeric meltblown layer may also be impregnated or saturated with a latex composition. Such a composition helps reduce particulate release from the meltblown layer and may also reduce abrasion. Various latexes may be used for impregnating the fibrous meltblown web and may include and acrylic lates, a nitrile rubber latex, a styrene butadiene rubber latex, a natural butadiene rubber latex, a high stretch acrylic elastomer latex and a polyurethane latex. Of these, the softer the polymeric binder (the saturant) such as the natural butadiene rubber, the lesser the impact on elongation and hand are believed to be. The nonelastic latexes (e.g.: acrylic), should improve tear strength of the web. The saturant need not be elastomeric, as long as the web retains an elastomeric property as defined above. An example of a commercially available latex useful in the practice of this embodiment of the invention is urethane latex UE-40-512 available from Permuthane, Inc.

The saturation of a fabric is well known in the art and may be done for example, by spraying the saturant solution onto one or both sides of the web. Saturation of the fabric may also be accomplished by dipping the web into a bath of saturant and removing the excess liquid by passing the web through a nip roller arrangement. After saturation, the fabric is typically dried. Drying may be acheived by passing the fabric around a series of steam drums at a temperature appropriate for the particular saturant composition being used. This is within the knowledge of those skilled in the art.

Saturant total solids in the saturant composition may range from 10 to 60 weight percent, depending on the desired dry saturant pickup. Dry pickup ranges from 10 to 120 dry parts of saturant per 100 dry parts of fibrous web material by weight. Particularly satisfactory ranges of dry pickup are from 20 to 70 dry parts of saturant per 100 dry parts of fibrous web, and saturant total solids in a range of 20 to 40 weight percent in the saturant composition are used. Wet saturant pickup can range from about 50 to about 300 wet parts per 100 parts of fibrous web material by weight.

The continuous liquid impermeable film useful in this invention may be one such as that made from polyolefins, polyamides, polyesters, polyurethanes, polyethers, copolyesters, co-polyamides or urethanes. A particularly useful film is available from the Dupont Company of Wilmington, Del., as Hytrel 8171 and is co-polyester. The film layer present in the laminate of this invention lends improved wind resistance and improved barrier properties to the laminate. It is believed, though the inventor does not wish to be bound by this belief, that the provision of a meltblown layer adjacent to the film layer provides greater structural integrity than the film alone would possess and therefore allows a thinner film layer to be used.

The liquid permeable layer may be a woven or knit fabric or a nonwoven fabric. Fibers and yarns can be synthetics such as polyester or nylon or natural fibers such as cotton or wool, or blends of synthetic and natural fibers. A particularly useful liquid permeable layer is Mallon cloth, which is a 100% texturized polyester jersey knit available from Acme Mills, of Detroit, Mich. A still more useful liquid permeable layer is polyamide (nylon) tricot knit available from Mantex Corp. of New York, N.Y. in style number S850. The polyamide in S850 is nylon 6.

A fabric according to this invention may be prepared by adhesively laminating the layers together. For example, the film may be unwound from the roll upon which it comes from the manufacturer and adhesively laminated to either the permeable layer or the elastomeric meltblown layer. This two layer laminate may then be adhesively joined to the remaining layer. Any other method known to those skilled in the art to be effective may be used, such as, for example, thermal bonding, print bonding and ultrasonic bonding. The applicants have found adhesive lamination to be satisfactory and have used a cross-linked urethane adhesive, available from Shawmut Mills of West Bridgewater, Mass.

The properties of various laminates were compared. These laminates are described in Table 1 where only Sample H is a laminate made in accordance with this invention.

TABLE 1

| Sample | Description |
|---|---|
| A | Laminate of a 1.4 ounce/square yard (osy) spunbond/meltblown/spunbond (SMS) Evolution ® III fabric with a 0.75 mil EVA film hot melt adhesively laminated thereto. The spunbond layers were each 0.5 osy and the meltblown layer 0.4 osy. Evolution ® III fabric is available from the Kimberly-Clark Corporation of Dallas, Texas. |
| B | Laminate of a 1.4 osy SMS Evolution ® III fabric with a 1 mil film of Hytrel G4778 resin hot melt adhesively laminated thereto. The spunbond layers were each 0.5 osy and the meltblown layer 0.4 osy. |
| C | Laminate of a 1.4 osy SMS Evolution ® III fabric with a 1 mil film of Deerfield PT 6100S polyurethane, solvent based adhesively laminated thereto. The spunbond layers were each 0.5 osy and the meltblown layer 0.4 osy. The polyurethane film was manufactured by Deerfield Urethane, Inc. |
| D | Laminate of a 1.4 osy SMS Evolution ® III fabric with a 1 mil film of Morthane PB364-200 polyurethane, solvent based adhesively laminated thereto. The spunbond layers were each 0.5 osy and the meltblown layer 0.4 osy. The polyurethane film was manufactured by Argotech, Inc. |
| E | Tightly woven 100% polyester yarn. Manufactured by Precision Fabrics Group of Greensboro, N.C., and available in the form of a surgical gown under the trade name Compel ® available from the Standard Textile Co., Inc. |
| F | Woven 100% polyester fabric with an expanded PFE membrane attached thereto. Manufactured by W. L Gore & Associates of Newark, Delaware, and available as a surgical gown under the trade name Gore-tex ® . |
| G | Laminate of nylon tricot knit, 1 mil Hytrel 8171 film, nylon tricot knit. |
| H | Laminate made in accordance with this invention using 1 osy elastomeric meltblown fabric according to Boggs (U.S. Pat. No. 4,707,398) using Arnitel EM-400 polyetherester available from DSM of Sittard, Holland, 1 mil Hytrel 8171 film and polyamide (nylon) tricot knit available from Mantex Corp. of New York, New York in style number S850. |

The above described laminates were subjected to tests for hand properties, and thermal and moisture transmission.

The hand properties were measured according to the Kawabata Evaluation System (KES) which is known to those skilled in the art and described in chapter four of "The Standardization and Analysis of Hand Evaluation", 2nd Edition, (1980) by S. Kawabata and M. Niwa and available from the Hand Evaluation and Standardization Committee of the Textile Machinery Society of Japan, (Osaka). This system includes tests for compression, tensile, shear, bending, and surface properties as a method to quantify those things which make a material feel a particular way.

The compressibility of a 2 square centimeter area was measured with a KES-FB3 instrument. The EMC is the compressibility at 50 gf/cm2 compared to the initial thickness measured at 0.5 gf/cm2, in percent. A higher compressibility EMC value indicates greater compressibility.

The tensile test measures the stress/strain parameters of the sample and is performed on a KES-FB1 instrument. The tensile EMT indicates the extensibility of the material and is the percent strain at maximum load of 500 gf/cm. A higher tensile EMT indicates greater extensibility.

The shear testing measures the shear stiffness in gf/cm degree of the sample and is performed on a KES-FB1 instrument. Opposing parallel forces are applied to the fabric until a maximum offset angle of 8° is reached. A tension load of 10 gf/cm was applied to the specimen for the shear testing. Shear stiffness (G) is the ease with which yarns or fibers slide against one another. A higher G value means greater stiffness or resistance to the shearing movement.

The bending test measures the bending rigidity per unit fabric width (B) in gf cm2/cm and is performed on the KES-FB2 instrument. A higher B value indicates greater stiffness or resistance to bending.

The surface properties of the materials was determined using a KES-FB4 Surface tester. A high geometric roughness (SMD) in microns corresponds to a geometrically rough surface.

The compilation of the data from the above tests is given in Table 2 for the samples of Table 1.

TABLE 2

| Sample | Tensile EMT | Shear G | Bending B | Surface SMD | Compression EMC |
|---|---|---|---|---|---|
| A | 2.51 | 4.64 | 0.12 | 5.39 | 16.6 |
| B | 2.08 | 5.14 | 0.18 | 4.74 | 17.1 |
| C | 4.95 | 4.27 | 0.10 | 5.42 | 21.0 |
| D | 6.16 | 4.22 | 0.14 | 5.16 | 27.6 |
| E | 3.83 | 2.66 | 0.10 | 1.87 | 22.1 |
| F | 11.87 | 3.03 | 0.13 | 12.21 | 21.1 |
| G | 26.79 | 2.83 | 0.06 | 15.7 | 20.0 |
| H | 10.41 | 2.64 | 0.06 | 13.1 | 35.1 |

The data from Table 2 indicates that the fabric made in accordance with this invention has excellent compression and tensile properties and good shear, bending and surface properties.

The thermal properties of the materials were measured in order to calculate comfort limits according to the Kawabata Thermolabo thermal analyzing system which is known in the art. This calculates the activity level in Watts/square meter with a minimum (Min) level being that which could be sustained while maintaining a dry skin surface, an upper comfort (Com) level being defined by sweat evaporation over twenty percent of the body surface area, and a maximum (Max) level being that which indicates the maximum level of activity what could be exerted with 100% of the skin wetted before significant heat stress is experienced.

The compilation of the comfort data from the above tests is given in Table 3 for the samples of Table 1.

TABLE 3

| | Comfort | | |
| Sample | Min | Com | Max |
|---|---|---|---|
| A | 126 | 150 | 242 |
| B | 123 | 154 | 277 |
| C | 122 | 150 | 262 |
| D | 122 | 168 | 351 |
| E | 129 | 187 | 421 |
| F | 126 | 179 | 394 |
| G | 131 | 204 | 498 |
| H | 128 | 193 | 452 |

The data from Table 3 indicates that the fabric according to this invention provides good comfort to the wearer during exertion.

The moisture vapor transmission properties of the materials were measured to determine the rate of steady state water vapor transmission through each material. In this procedure, the sample is sealed at the top of a cup of water (100 mls) and placed in a 100° F. controlled environment for 24 hours. The difference in beginning and ending cup weights is used to calculate the moisture vapor transmission rate (MVTR) in gm/square meter/24 hours. A garment made from a higher MVTR fabric would be more comfortable for the wearer since in would allow sweat to be shed from the body more readily than one made from a lower MVTR fabric.

The compilation of the MVTR data from the above test is given in Table 4 for the samples of Table 1.

TABLE 4

| Sample | MVTR |
|---|---|
| A | 193.00 |
| B | 2033.36 |
| C | 1496.44 |
| D | 2763.03 |
| E | 6406.85 |
| F | 4304.13 |
| G | 4056.67 |
| H | 4165.33 |

The data from Table 4 indicates that the fabric according to this invention provides good comfort to the wearer. Further, it has been found that a laminate according to this invention provides a higher MVTR than a laminate without the elastomeric meltblown layer. For example, it has been found that a laminate like sample H will have an MVTR of at least 10% greater than, and up to more than twice that, of an identical laminate without the elastomeric meltblown layer. The reason for this improvement is not entirely understood by the inventors though it is believed to be at least partially attributable to improved moisture distribution by the meltblown nonwoven layer.

Since these materials are contemplated to be used as surgical gowns (among other applications), a further informative test for materials of this type was performed. The test measures the amount of liquid transmission allowed. This test is referred to as blood strikethrough and gives an indication of the amount of blood which will be passed through the fabric according to test method ASTM 22. Table 5 contains the blood strikethrough data for the indicated samples.

TABLE 5

| Sample | % |
| --- | --- |
| A | 1.0 |
| E | 0.21 |
| H | 0.0 |

The data from Table 5 indicates that the fabric of this invention provides good protection against blood permeability and provides a blood strikethrough below that of commercially available Compel® fabric. The fabric of this invention is generally below 1.0% blood strikethrough.

A further useful property of the fabric of this invention is that found during the construction of a garment such as a surgical gown.

A surgical gown consists of a number of parts such as the front, back, sides, sleeves, etc. and which may themselves consist of a number of parts. While a gown may be engineered in such a way as to minimize the number of parts, some attaching or joining of parts is generally unavoidable in normal gown construction. During such construction the barrier properties of the fabric may be compromised by the method of joining the parts together. For example, conventional stitching of the arms onto the main body of the gown would result in puncturing the barrier layer of the fabric.

The fabric of this invention helps avoid this problem by the provision of a heat sealable layer on an outer surface. Specifically, the elastomeric meltblown layer may be joined to another layer by the application of heat to slightly soften the layers of different pieces, e.g. garment sleeves and torso, in contact so that upon cooling they remain as one piece. The exact temperature at which this heat sealing must be performed will depend on the polymers used for the various layers and are within the skill of those in the art to determine.

Yet another useful property of the fabric of this invention is that it may be reused a number of times before being disposed of. Such reusability helps reduce disposal costs and environmental problems when the fabric is used as a surgical gown, for example, since materials contaminated with bodily fluids require specialized disposal procedures. By reducing the volume of material which must be disposed of relative to single use materials, surgical garments made from the fabric of this invention can contribute to a reduction in national health care expenditures. Table 6 indicates which of the materials from Table 1 are considered reusable or single use fabrics, reusable fabrics being those which may be laundered and used again for the same purpose as originally. The number of re-uses varies, but typically is in a range of 25 to 100 times.

TABLE 6

| Single Use | Reusable |
| --- | --- |
| A, B, C, D | E, F, G, H |

If additional or enhanced properties are required for more specialized uses of the fabric of this invention, the fabric may be treated with chemicals such as water repellant chemicals, softening chemicals, fire retardant chemicals, oil repellent chemicals and mixtures thereof. These types of chemicals are conventional and known to those skilled in the art of treating fabrics as are the methods of chemical application to fabrics. Treating methods include for example, spraying, and immersion.

The data from the preceding discussion indicate that the fabric of this invention provides good hand, comfort, moisture transmission and protection against fluid transmission. This novel fabric also provides the ability to use heat-sealable seams in the production of garments made from the fabric and provides reusability in such garments.

I claim:

1. A protective laminate comprising in this order:

a first layer of a elastomeric meltblown thermoplastic polyetherester web wherein said polyetherester has the general formula:

$$H-([O-G-C(=O)-C_5H_4-C(=O)]-[O-(CH_2)_a-O-C(=O)-C_6H_4-C(=O)]_m)_n-O-(CH_2)_a-OH$$

where "G" is selected from the group consisting of poly(oxyethylene)-alpha,omega-diol, poly(oxypropylene)-alpha,omega-diol, poly(oxytetramethylene)-alpha,omega-diol and "a", "m" and "n" are positive integers;

a second layer of liquid impermeable film, wherein said film is a polyetherester, and;

a third layer of liquid permeable nylon tricot knit material, wherein said layers are adhesively bonded together, and;

wherein said laminate has a MVTR at least 10% higher than an identical laminate without said elastomeric meltblown web layer.

2. The protective laminate of claim 1 which is present in a surgical gown having seams wherein said laminate is converted into a surgical gown by heat-sealing said seams.

* * * * *

UNITED STATES PATENT AND TRADEMARK OFFICE
CERTIFICATION OF CORRECTION

PATENT NO. : 5,520,980

DATED : May 28, 1996

INVENTOR(S): Linda J. Morgan; Robert D. Harris, Jr.

It is certified that errors appears in the above-identified patent and that said Letters Patent is hereby corrected as shown below:

Column 10, line 9, "repellant", should read --repellent--;
Column 10, line 29, "$C_5$", should read --$C_6$--.

Signed and Sealed this

Thirty-first Day of December, 1996

Attest:

BRUCE LEHMAN

*Attesting Officer*     *Commissioner of Patents and Trademarks*